United States Patent
Carter et al.

(10) Patent No.: US 9,307,891 B2
(45) Date of Patent: Apr. 12, 2016

(54) ENDOSCOPE ROTATIONAL AND POSITIONING APPARATUS AND METHOD

(75) Inventors: Matthew P. Carter, Dobson, NC (US); Brian K. Jones, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 767 days.

(21) Appl. No.: 11/796,525

(22) Filed: Apr. 27, 2007

(65) Prior Publication Data

US 2007/0265497 A1 Nov. 15, 2007

Related U.S. Application Data

(60) Provisional application No. 60/797,123, filed on May 3, 2006.

(51) Int. Cl.
| | | |
|---|---|---|
| *A61B 1/00* | (2006.01) |
| *A61B 1/04* | (2006.01) |
| *A61M 16/00* | (2006.01) |
| *A62B 9/06* | (2006.01) |
| *A61B 19/00* | (2006.01) |
| *A61B 1/24* | (2006.01) |
| *A61B 17/34* | (2006.01) |

(52) U.S. Cl.
CPC ........... *A61B 1/0014* (2013.01); *A61B 1/00039* (2013.01); *A61B 1/00149* (2013.01); *A61B 1/00154* (2013.01); *A61B 1/24* (2013.01); *A61B 19/26* (2013.01); *A61B 2017/347* (2013.01)

(58) Field of Classification Search
CPC ........... A61B 1/00131; A61B 1/00133; A61B 1/00147; A61B 1/00154; A61B 1/0016; A61B 1/267; A61B 1/2673; A61B 1/2676; A61B 1/273; A61B 1/2733; A61B 1/27736; A61B 1/31
USPC ......... 600/102, 114, 120, 121, 125, 128, 124, 600/195; 128/861, 200.26, 207.14; 606/195
See application file for complete search history.

(56) References Cited

U.S. PATENT DOCUMENTS

| | | | |
|---|---|---|---|
| 4,024,858 A | 5/1977 | Chikama | |
| 4,112,936 A | 9/1978 | Blachly | |
| 4,530,354 A * | 7/1985 | Froilan | .................... 128/207.17 |
| 5,402,776 A | 4/1995 | Islava | |
| 5,496,260 A | 3/1996 | Krauter et al. | |
| 5,496,282 A | 3/1996 | Militzer et al. | |

(Continued)

FOREIGN PATENT DOCUMENTS

| | | |
|---|---|---|
| EP | 0 667 126 B1 | 7/1994 |
| JP | 55-32761 | 3/1980 |

(Continued)

OTHER PUBLICATIONS

International Search Report for International Application No. PCT/US2007/010314, dated Feb. 28, 2008, 6 pages.

(Continued)

*Primary Examiner* — Ryan Henderson
(74) *Attorney, Agent, or Firm* — Brinks Gilson & Lione

(57) ABSTRACT

An endoscope securing and positioning device is provided for adjusting or maintaining the position of an endoscope. The device allows the medical professional to easily rotate an endoscope or maintain its position without having to maintain a grip on the endoscope.

2 Claims, 19 Drawing Sheets

(56) References Cited

U.S. PATENT DOCUMENTS

| | | | |
|---|---|---|---|
| 5,505,714 A * | 4/1996 | Dassa et al. | 604/534 |
| 5,626,128 A | 5/1997 | Bradley et al. | |
| 5,674,182 A * | 10/1997 | Suzuki et al. | 600/129 |
| 6,029,668 A | 2/2000 | Freed | |
| 6,286,555 B1 | 9/2001 | Pauker et al. | |
| 6,461,372 B1 | 10/2002 | Jensen et al. | |
| 6,517,549 B1 * | 2/2003 | Dennis | 606/108 |
| 6,673,012 B2 | 1/2004 | Fujii et al. | |
| 6,719,685 B2 * | 4/2004 | Fujikura et al. | 600/114 |
| 6,840,238 B1 * | 1/2005 | Van Hegelsom | 128/201.22 |
| 6,851,424 B2 | 2/2005 | Scopton | |
| 2002/0162555 A1 | 11/2002 | West et al. | |
| 2003/0191486 A1 | 10/2003 | Griego et al. | |
| 2003/0229338 A1 * | 12/2003 | Irion et al. | 606/1 |
| 2005/0203336 A1 | 9/2005 | Seki et al. | |

FOREIGN PATENT DOCUMENTS

| | | |
|---|---|---|
| JP | 59-181122 | 10/1984 |
| JP | 62-70501 | 5/1987 |
| JP | 62-192135 | 8/1987 |
| JP | 1-148233 | 6/1989 |
| JP | 2001-275942 | 10/2001 |
| WO | WO 02/076541 A1 | 10/2002 |
| WO | WO 2004/007009 A1 | 1/2004 |
| WO | WO 2004/032730 A1 | 4/2004 |
| WO | WO 2005/099558 A1 | 10/2005 |

OTHER PUBLICATIONS

Written Opinion of the International Searching Authority for International Application No. PCT/US2007/010314, dated Feb. 28, 2008, 9 pages.

European Patent Office's Examination Report for corresponding European Application 07 776 403.3, dated Nov. 26, 2013, 2p.

Canadian Intellectual Property Office Examiner's Report Office Action for U.S. Pat. No. 2,651,081,dated Dec. 24, 2010, 3 pages.

Jun. 3, 2011 Response to the Canadian Intellectual Property Office Examiner's Report Office Action for U.S. Pat. No. 2,651,081,dated Dec. 24, 2010, 8 pages.

European Patent Office Communication dated Apr. 29, 2010, 4 pages.

Office Action from corresponding JP Application No. 2009-509627 with English translation, dated Jun. 18, 2014, 7p.

* cited by examiner

ENDOSCOPE ROTATIONAL AND POSITIONING APPARATUS AND METHOD

RELATED APPLICATIONS

The present patent document claims the benefit of the filing date under 35 U.S.C. §119(e) of Provisional U.S. Patent Application Ser. No. 60/797,123, filed May 3, 2006, which is hereby incorporated by reference in its entirety.

FIELD OF THE INVENTION

This invention relates to endoscopes used generally for visual examination of a body.

BACKGROUND OF THE INVENTION

Endoscopes are primarily used to visually examine parts of the body including the stomach, colon, intestine, and esophagus. In order to view an inner portion of the body, the medical professional will insert the endoscope into a patient through an orifice.

At the handle portion of the endoscope are a number of controls for deflecting the tip of the endoscope that is within the patient. Such deflection allows the medical professional to better view the bodily interior. The medical professional normally manipulates the control features of the endoscope by holding the handle at chest level with his/her right hand.

In addition to deflecting the tip of the endoscope by using the control handle, the medical professional also rotates the endoscope in order to move to and better view an area of the bodily interior. For example, when used orally, the medical professional rotates the device by having his/her free hand hold a portion of the endoscope just outside the patient's mouth and turning his/her hand from side-to-side. It is difficult for the medical professional to turn the endoscope to any great degree because the medical professional is limited by the degree of rotation that his/her wrist can turn. Once the medical professional reaches that limit, the medical professional must stop and re-grip the endoscope in order to further rotate the device.

A medical professional can also rotate the device by fully extending the potion of the endoscope that remains outside the patient and then turning the device by twisting the hand that is holding the handle of the endoscope. However, the medical professional has less precision when rotating the device in this manner.

The medical professional cannot maintain the rotated position of the endoscope without using his/her hand (or another person's hand) to hold the endoscope in place. This results in the medical professional losing the ability to perform other functions with that hand.

BRIEF SUMMARY OF THE INVENTION

A medical device for use with an endoscope having a handle and an elongated tubular portion extending from the handle is provided. The medical device includes an attachment portion adapted for attachment to the elongated tubular portion of the endoscope, the attachment portion including one of means for adjusting and means for securing the rotational position of the elongated tubular portion of the endoscope.

Additionally, a medical device for use with an endoscope having a handle and an elongated tubular portion extending from the handle is provided. The medical device includes an attachment portion adapted for attaching to the elongated tubular portion of the endoscope. The attachment portion includes means for rotating the elongated tubular portion of the endoscope.

Further, a medical device for use with an endoscope having a handle and an elongated tubular portion extending from the handle is provided. The medical device includes a bite block having a proximal portion, a distal portion, an inner portion, and an outer portion. The inner portion contains a lumen. The lumen has an inner diameter that is greater than the outer diameter of the elongated tubular portion of the endoscope. The lumen is adapted to laterally receive the elongated tubular portion of an endoscope.

Additionally, a medical device for use with an endoscope having a handle and an elongated tubular portion extending from the handle is provided. The medical device includes a belt and a clamp connected to the belt. The clamp is adapted to movably secure the elongated tubular portion of the endoscope.

Furthermore, a medical device for use with an endoscope having a handle and an elongated tubular portion extending from the handle is provided. The medical device includes a cable having a proximal portion and a distal portion. The distal portion is attached to the elongated tubular portion of the endoscope. The medical device also includes a control device. The proximal portion of the cable is attached to the control device. The control device is adapted to control movement of the cable. The cable is adapted to control the movement of the elongated tubular portion of the endoscope.

Additionally, a medical device for use with an endoscope having a handle and an elongated tubular portion extending from the handle is provided. The medical device includes a proximal portion configured to laterally receive and adjustably maintain a position of the elongated tubular portion of the endoscope and a distal portion configured to attach to a stable object.

Furthermore, a medical device for maintaining the torque of an endoscope is provided. The medical device includes an endoscope having a handle, a proximal elongated tubular portion extending from the handle, and a distal elongated tubular portion being rotatable relative to the proximal elongated tubular portion. The medical device further includes a coupling; wherein the coupling is fixedly connected to one of the proximal elongated tubular portion of the endoscope and the distal elongated tubular portion of the endoscope; and wherein the coupling is releasably connected to the other of the proximal elongated tubular portion of the endoscope and the distal elongated tubular portion of the endoscope.

In addition, a medical device for use with an endoscope having a handle and an elongated tubular portion extending from the handle is provided. The medical device includes a cuff adapted to fit around a portion of the elongated tubular portion extending from the handle and a locking mechanism adapted to retain the position of the cuff with respect to the elongated tubular portion of the endoscope.

Furthermore, a method of maintaining the torque of an endoscope is provided. The method includes providing a device for maintaining the torque of an endoscope. The device includes a position engagement device adapted to maintain the position of an endoscope and a position disengagement device adapted to release the position of an endoscope. The method also includes positioning the endoscope within a patient and engaging the position engagement device.

BRIEF DESCRIPTION OF THE SEVERAL VIEWS OF THE DRAWINGS

The embodiments will be further described in connection with the attached drawing figures. It is intended that the drawings included as a part of this specification be illustrative of the embodiments and should in no way be considered as a limitation on the scope of the invention.

FIG. 1A is a side-view of a patient depicting a use of an endoscope positioning device.

DETAILED DESCRIPTION OF PRESENTLY PREFERRED EMBODIMENTS

Figure 1A:
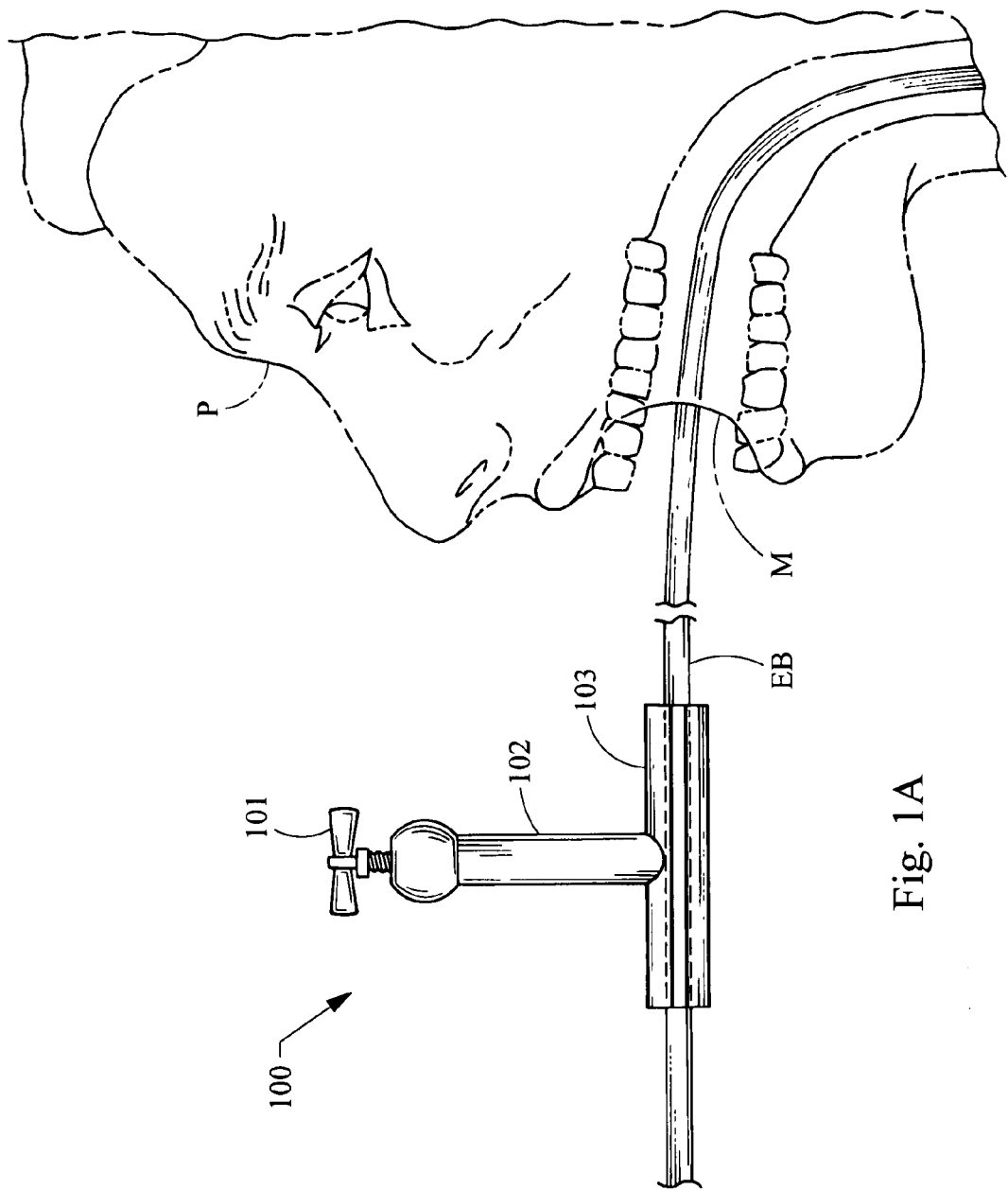
FIG. 1B is a perspective view of an endoscope positioning device.

The exemplary embodiments disclosed herein allow a medical professional to rotate an endoscope and/or maintain the rotated position of the endoscope.

A more detailed description of the embodiments will now be given with reference to FIGS. 1A-15. Throughout the disclosure, like reference numerals and letters refer to like elements. The present invention is not limited to the embodiments illustrated; to the contrary, the present invention specifically contemplates other embodiments not illustrated but intended to be included in the claims.

Figure 1B:
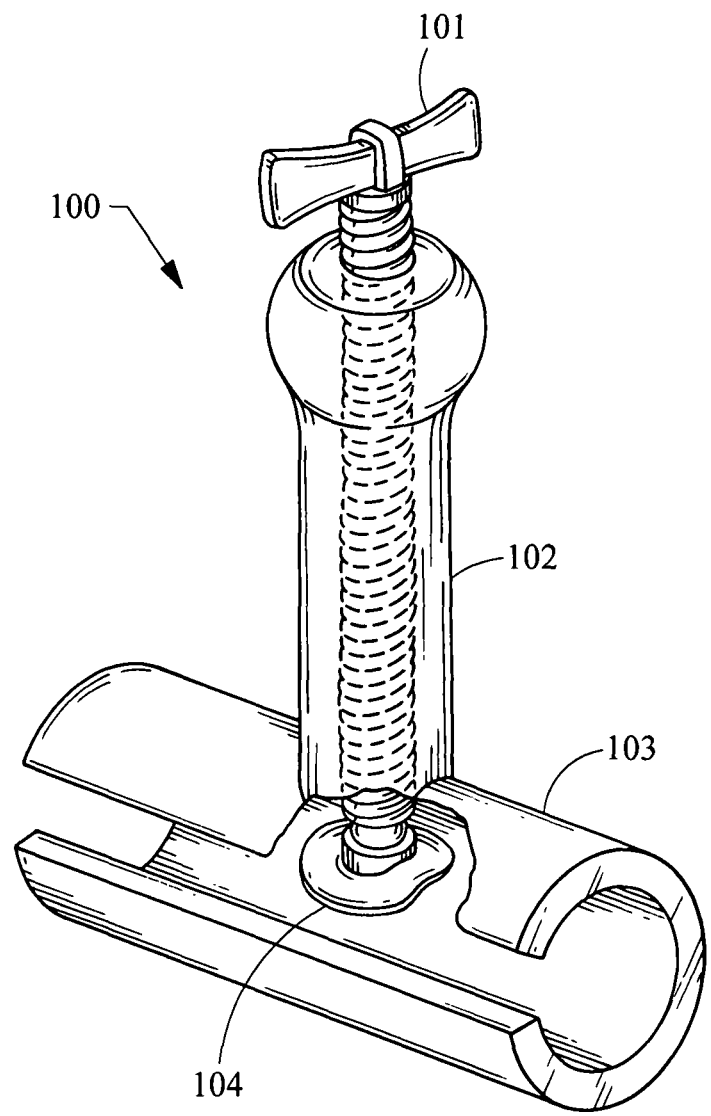

FIGS. 1A and 1B depict an endoscope positioning device 100 that aids in positioning and twisting an endoscope by giving the medical professional more leverage. Endoscope positioning device 100 includes an arm 102 that is pulled, pushed, or otherwise manipulated in order to rotate the endoscope. Endoscope positioning device 100 is attached to elongated tubular body EB (show in FIG. 1A) of endoscope via removable cuff 103 that slips over elongated tubular body EB of endoscope. Adjustable screw 101 is used to secure cuff 103 to elongated tubular body EB of endoscope. Adjustable screw 101 has a pad 104 (shown in FIG. 1B) that frictionally engages endoscope without damaging the outer service of elongated tubular body EB of endoscope. Devices other than an adjustable screw 101 are also contemplated, including, but not limited to, a spring-loaded peg. Screw 101, arm 102, and cuff 103 can made from a variety of materials, including but not limited to, stainless steel, polyurethane, polytetrafluoroethylene, other suitable polymers, and other suitable materials.

To use endoscope positioning device 100, the medical professional places cuff 103 around elongated tubular body EB of endoscope. Screw 101 is tightened such that pad 104 (shown in FIG. 1B) applies sufficient pressure to elongated tubular body EB of endoscope to prevent movement of cuff 103 with respect to elongated tubular body EB of endoscope. To rotate the endoscope, the medical professional pulls or pushes arm 102. Use of endoscope positioning device 100 is not limited to those endoscopes that enter through the mouth.

Figure 2:
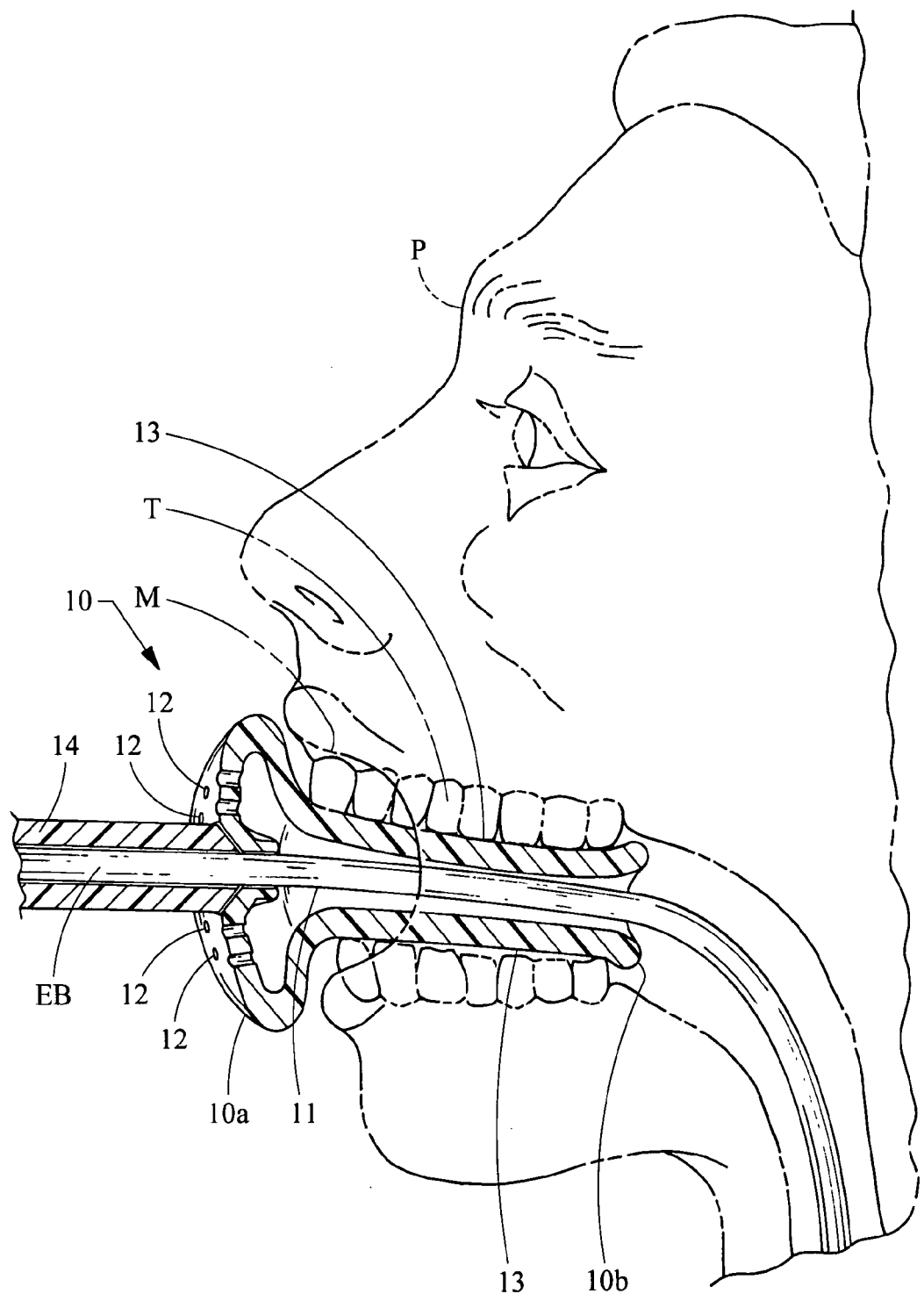
FIG. 2 is a side-view of a patient depicting a use of an endoscope securing and positioning device.

FIG. 2 is a side-view of a patient depicting a use of endoscope securing and positioning device 10. Endoscope securing and positioning device 10 is placed into mouth M of patient P and has a proximal portion 10A and a distal portion 10B. Endoscope securing and positioning device 10 maintains the rotation of an endoscope and also provides protection to elongated tubular body EB of the endoscope from teeth T of patient P. Patient P bites upon the outer portion 13 of endoscope securing and positioning device. Outer portion 13 of endoscope securing and positioning device 10 can be made from any medically acceptable material that is resistant to being damaged by pressure exerted from the mouth M of patient P using teeth T. Such materials include, but are not limited to polyurethane, polytetrafluoroethylene, other suitable polymers, and other suitable materials.

The inside of endoscope securing and positioning device 10 contains a lumen 11 having a diameter that is slightly larger than the outer diameter of elongated tubular body EB of the endoscope in order to allow elongated tubular body EB of the endoscope to pass there through. Endoscope securing and positioning device 10 also includes air holes 12 so that patient P can breathe through mouth M.

To use endoscope securing and positioning device 10, the medical professional places endoscope securing and positioning device 10 into mouth M of patient P such that distal portion 10B is nearest to the esophagus of patient P. Cuff 14 is placed around elongated tubular body EB of endoscope. Cuff 14 is a machined thermal plastic wedge-shaped attachment, however, it may also be made from a variety of other materials, including but not limited to, metal, polycarbonate, ABS, epoxies, and diallyl phthalate. Cuff 14 is 4"-5" long; however, other dimensions are also contemplated. The portion of elongated tubular body EB of the endoscope having cuff 14 is threaded through lumen 11 of endoscope securing and positioning device 10 at proximal portion 10A and is positioned as needed. Cuff 14 is engaged with the sides of lumen 11 so as to create a frictional force upon cuff 14 resulting in the position of elongated tubular body EB being maintained.

In order to reposition elongated tubular body EB, cuff 14 is pulled in the proximal direction of lumen 11 in order to cause lumen 11 not to engage cuff 14. Without the frictional force, cuff 14 no longer maintains the position of elongated tubular body EB; cuff 14 looses from around elongated tubular body EB thereby allowing cuff 14 to be repositioned along elongated tubular body EB; and elongated tubular body EB is able to be repositioned with respect to patient P. Once elongated tubular body EB is repositioned, cuff 14 is wedged back into lumen 11 to secure and maintain the position of elongated tubular body EB. Lumen 11 is lined with a rubber (polyurethane, polytetrafluoroethylene, other suitable polymers, and other suitable materials may also be used) in order to prevent damage to elongated tubular body EB of endoscope as well as to increase friction there between.

Figure 3:
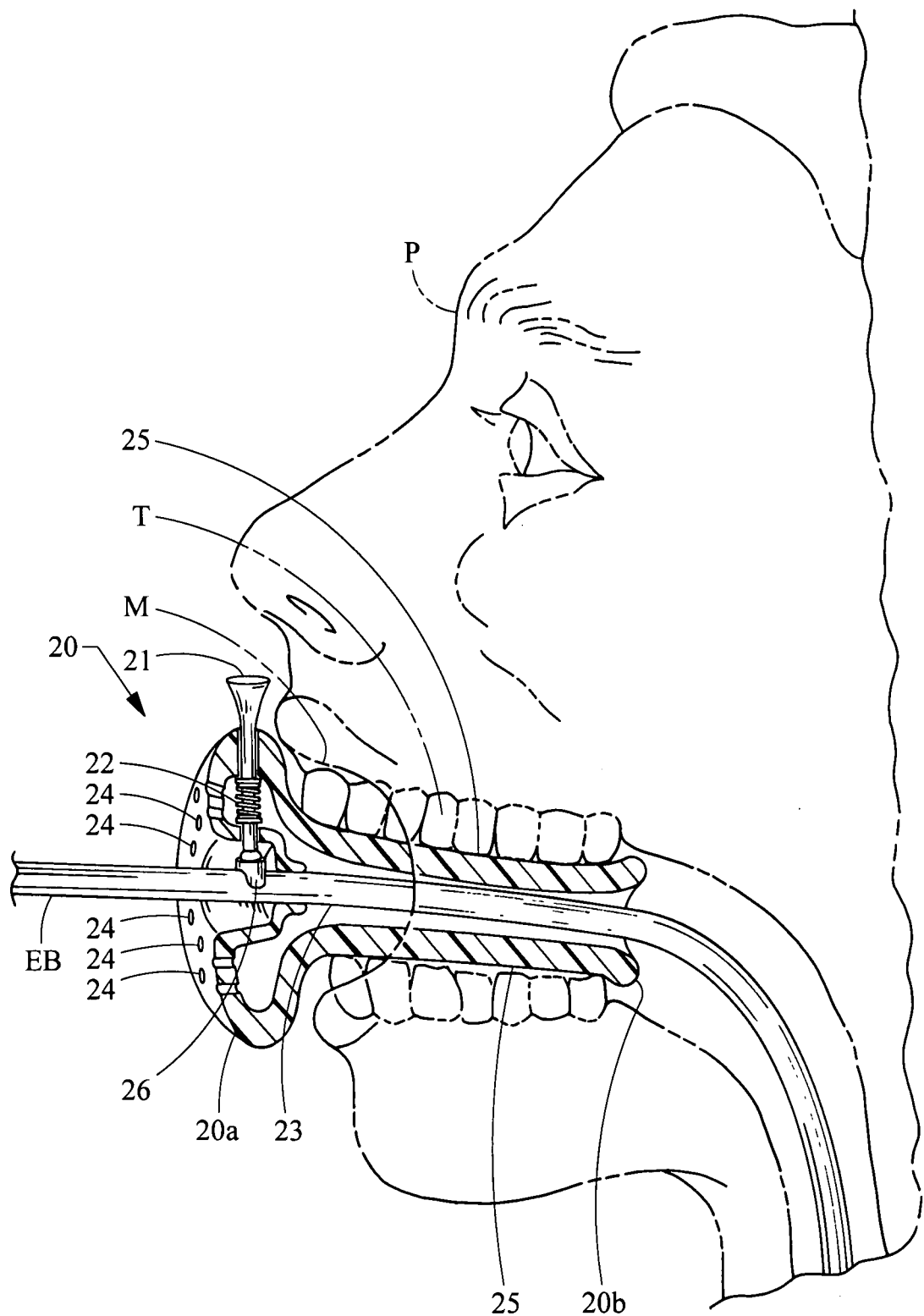
FIG. 3 is a side-view of a patient depicting a use of an endoscope securing and positioning device.

FIG. 3 depicts another endoscope securing and positioning device 20 similar to the one depicted in FIG. 2. In FIG. 3, endoscope securing and positioning device 20 has a proximal portion 20A and a distal portion 20B. Endoscope securing and positioning device 20 maintains the rotation of elongated tubular body EB of the endoscope and also protects elongated tubular body EB of the endoscope from damage due to teeth T of patient P. Air holes 24 are provided so that patient P can breath through mouth M.

Patient P bites down on outer portion 25 of endoscope securing and positioning device 20. Outer portion 25 of endoscope securing and positioning device 20 can be made from any medically acceptable material that is resistant to being damaged by pressure exerted from the mouth M of patient P using teeth T; polyurethane, polytetrafluoroethylene, other suitable polymers, and other suitable materials may be used. Endoscope securing and positioning device 20 has a lumen 23 having a diameter that is slightly larger than the outer diameter of elongated tubular body EB of the endoscope in order to allow elongated tubular body EB of the endoscope to pass there through. A spring loaded depressor 21, containing a spring 22, is used to maintain the position of elongated tubular body EB of the endoscope by applying pressure to the exterior of elongated tubular body EB of the endoscope so as to prevent lateral and rotational movement thereof. Depressor 21 can be made from any sturdy material, including, but not limited to, polyurethane, polytetrafluoroethylene, other suitable polymers, and other suitable materials. Spring 22 can be made from materials including, but not limited to, stainless steel. Tip of depressor 26 is contoured and lined with rubber (polyurethane, polytetrafluoroethylene, other suitable polymers, and other suitable materials may also be used) in order to prevent damage to elongated tubular body EB of endoscope as well as to increase friction there between. To disengage depressor 21, the medical professional pulls depressor 21 upward which releases elongated tubular body EB of endoscope. To engage depressor 21, the medical professional releases depressor 21 causing depressor 21 to apply pressure to the outer service of elongated tubular body EB.

Figure 4:
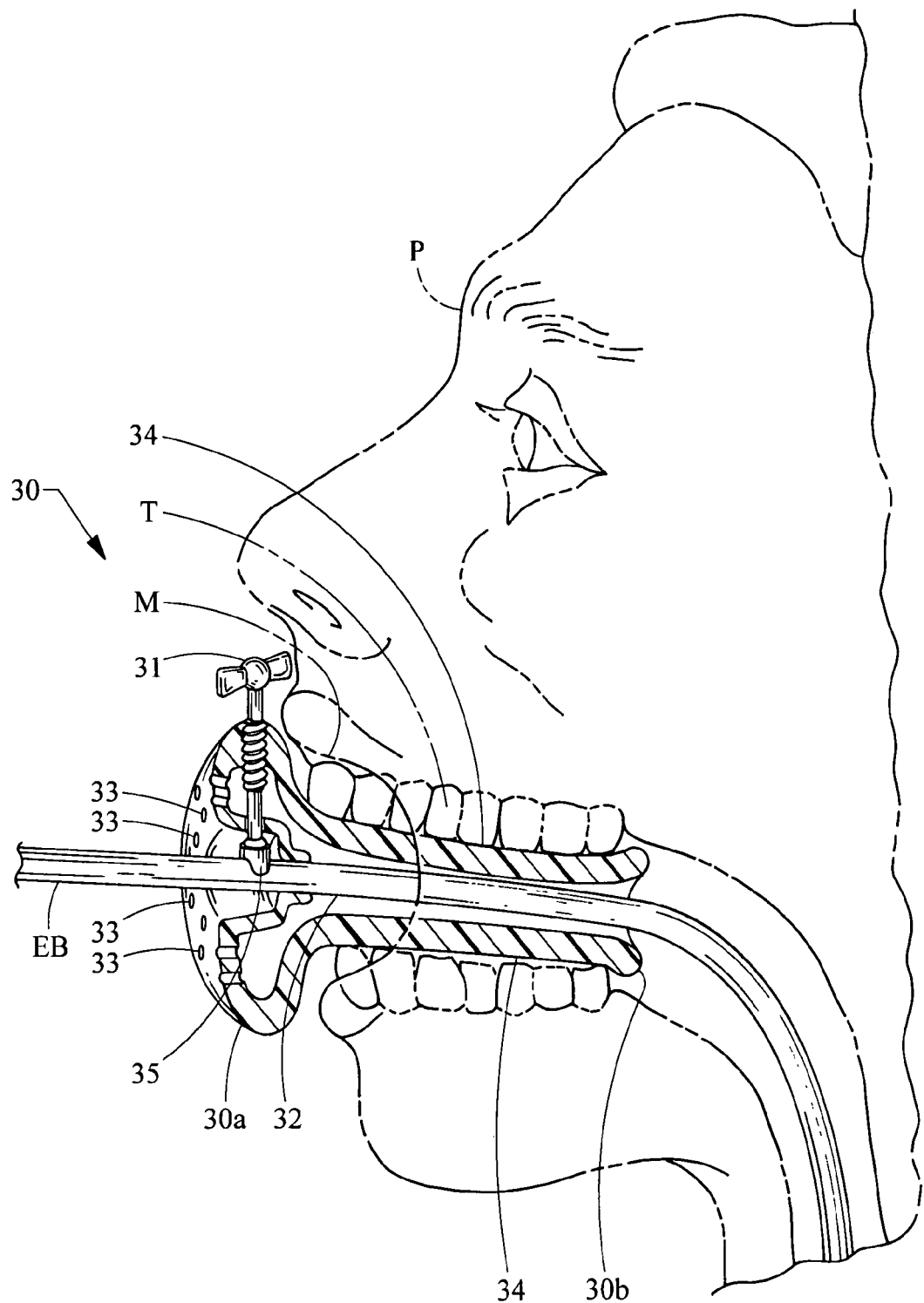
FIG. 4 is a side-view of a patient depicting a use of an endoscope securing and positioning device.

FIG. 4 depicts another endoscope securing and positioning device 30 that is similar to those depicted in FIGS. 2 and 3. In FIG. 4, endoscope securing and positioning device 30 has a proximal portion 30A and a distal portion 30B. Endoscope securing and positioning device 30 maintains the rotation of elongated tubular body EB of the endoscope and also protects elongated tubular body EB of the endoscope from damage due to teeth T of patient P. Air holes 33 are provided so that patient P can breath through mouth M.

Patient P bites down on outer portion 34 of endoscope securing and positioning device 30. Outer portion 34 of endoscope securing and positioning device 30 can be made from any medically acceptable material that is resistant to being damaged by pressure exerted from the mouth M of patient P using teeth T; polyurethane, polytetrafluoroethylene, other suitable polymers, and other suitable materials may also be used. Endoscope securing and positioning device 30 contains a lumen 32 having a diameter that is larger than the outer diameter of elongated tubular body EB of the endoscope in order to allow elongated tubular body EB of the endoscope to pass there through. A screw 31 is used to maintain the position of elongated tubular body EB of the endoscope by applying pressure on the exterior of elongated tubular body EB of the endoscope so as to prevent the lateral and rotational movement thereof. Screw 31 can be made from any sturdy material, including but not limited to, stainless steel. Screw 31 has a handle portion that is adapted to allow screw 31 to be rotated without having to use a screwdriver. Tip of screw 35 is contoured and lined with rubber (polyurethane, polytetrafluoroethylene, other suitable polymers, and other suitable materials may also be used) in order to prevent damage to elongated tubular body EB of endoscope as well as to increase friction there between.

When screw 31 is engaged, screw 31 holds elongated tubular body EB of the endoscope and prevents lateral and rotational movement of elongated tubular body EB of the endoscope. Therefore, because disengagement of screw 31 is necessary to adjust the position of elongated tubular body EB of the endoscope, the medical professional can maintain the position of elongated tubular body EB of the endoscope without needing to use a hand to hold elongated tubular body EB of the endoscope in the required position. To reposition elongated tubular body EB of the endoscope horizontally or rotationally, the medical professional disengages screw 31 by turning screw 31 counterclockwise until it releases the hold on elongated tubular body EB of the turning it clockwise until it engages and holds elongated tubular body EB of the endoscope in place.

Figure 5:
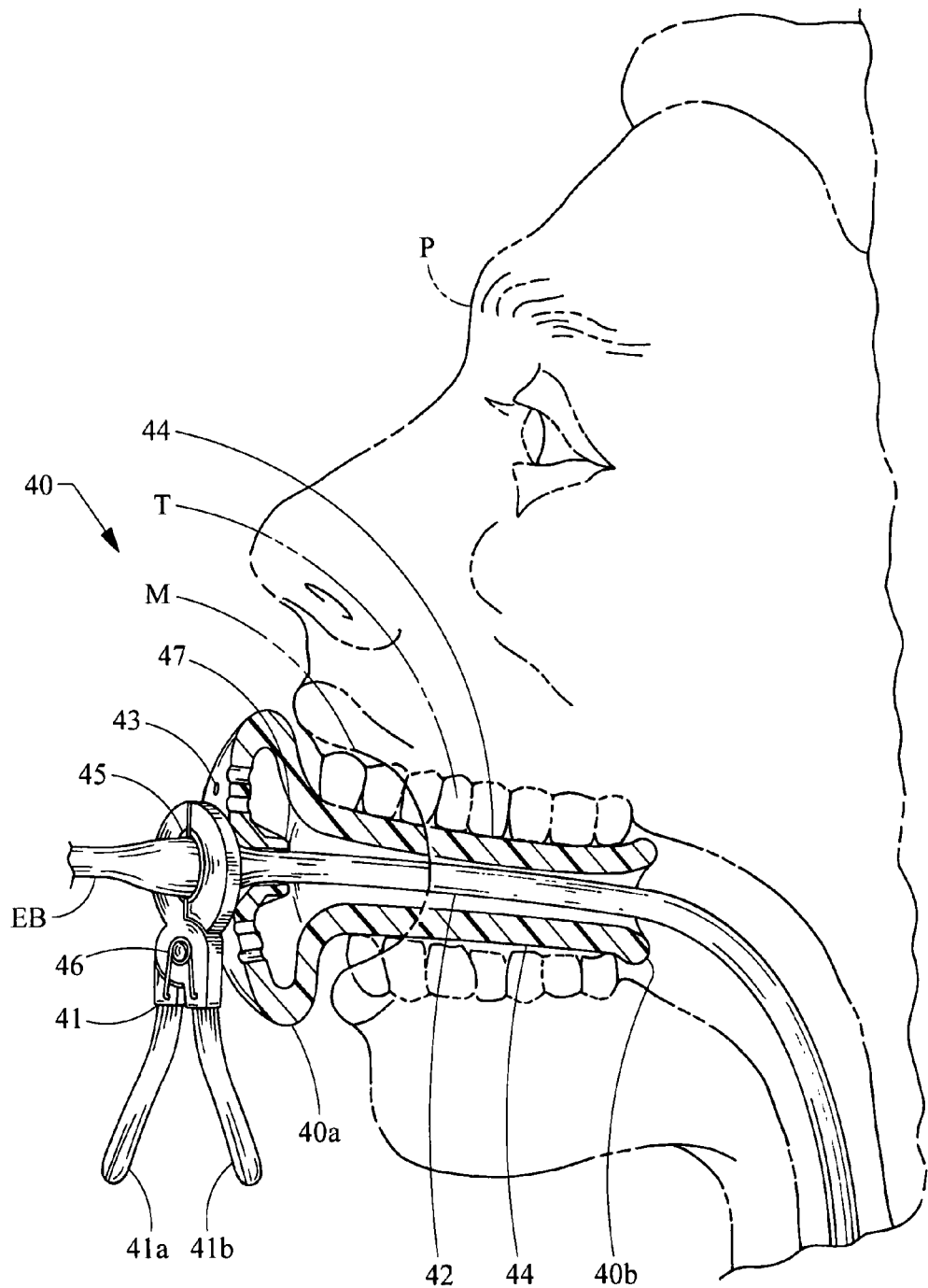
FIG. 5 is a side-view of a patient depicting a use of an endoscope securing and positioning device.

FIG. 5 depicts another endoscope securing and positioning device 40 similar to those depicted in FIGS. 2-4. Endoscope securing and positioning device 40 has a proximal portion 40A and a distal portion 40B. Endoscope securing and positioning device 40 maintains the rotation of elongated tubular body EB of the endoscope and also protects elongated tubular body EB of the endoscope from damage due to teeth T of patient P. Air holes 43 are provided so that patient P can breath through mouth M.

Patient P bites down on outer portion 44 of endoscope securing and positioning device 40. Outer portion 44 of endoscope securing and positioning device 40 can be made from any medically acceptable material that is resistant to being damaged by pressure exerted from the mouth M of patient P using teeth T; polyurethane, polytetrafluoroethylene, other suitable polymers, and other suitable materials may also be used. Endoscope securing and positioning device 40 contains a lumen 42 having a diameter that is larger than the outer diameter of elongated tubular body EB of the endoscope in order to allow elongated tubular body EB of the endoscope to pass there through.

Endoscope securing and positioning device 40 includes a clamp 41 that is used to maintain the position of elongated tubular body EB of the endoscope. Clamp 41 can be made from materials including, but not limited to, stainless steel. Spring 46 biases handles together to close clamp 41, such that clamp compresses elongated tubular body EB in order to maintain the position of the endoscope. To disengage clamps, the medical professional pulls apart clamp handles 41A, 41B. This releases clamp and allows the medical professional to reposition elongated tubular body EB. Clamp 41 is lined 45 with a rubber material (polyurethane, polytetrafluoroethylene, other suitable polymers, and other suitable materials may also be used) in order to prevent damage to elongated tubular body EB of endoscope as well as to increase friction there between.

Figure 6A:
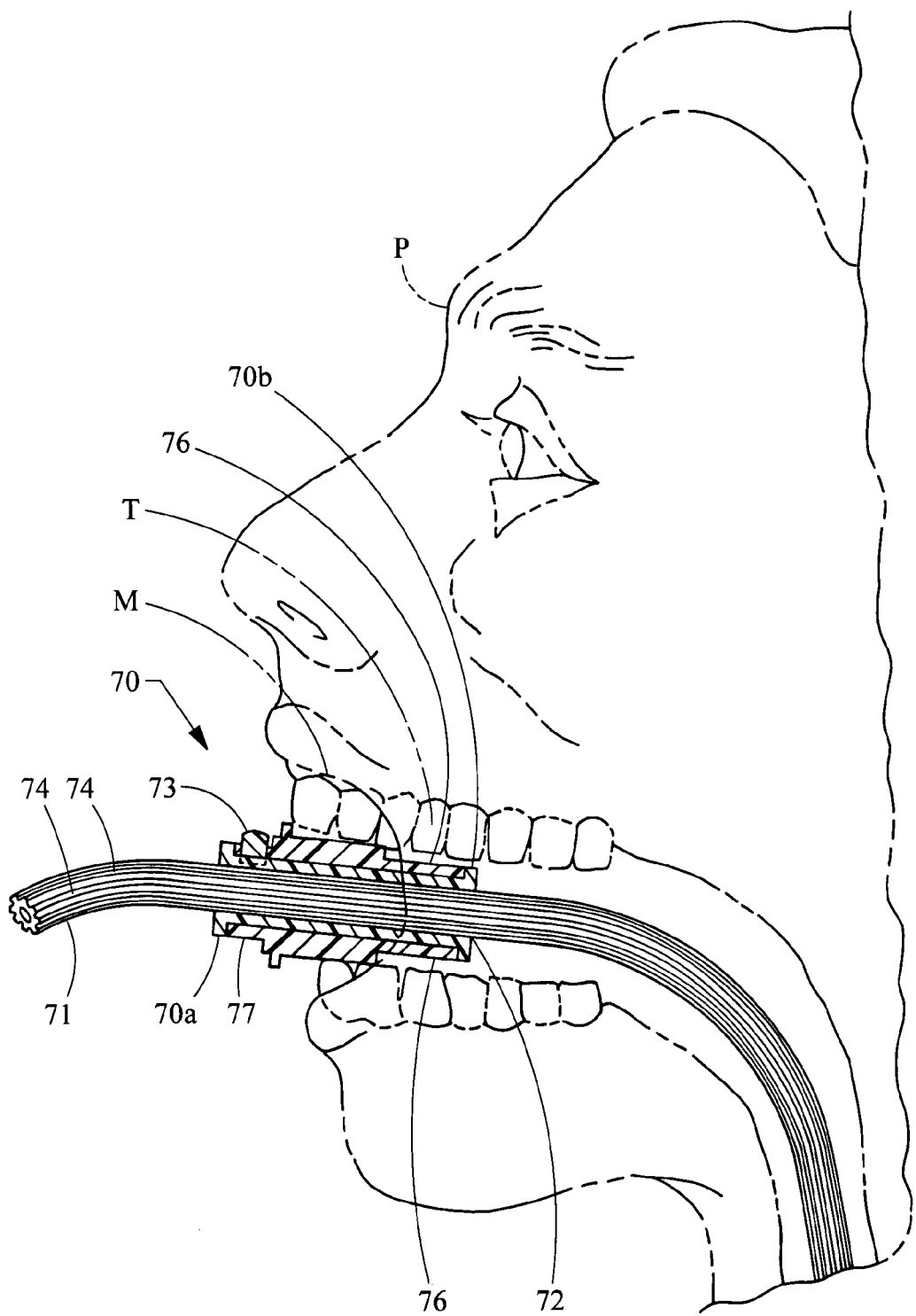
FIG. 6A is a side-view of a patient depicting a use of an endoscope securing and positioning device.
Figure 6B:
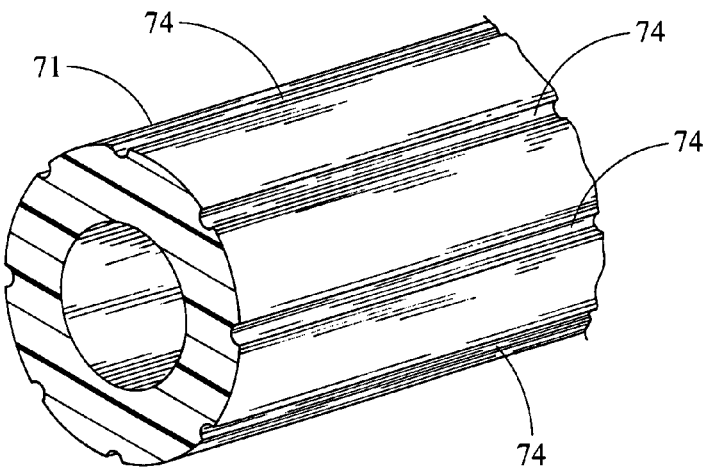
FIG. 6B is perspective view of a modified endoscope tube.
Figure 6C:
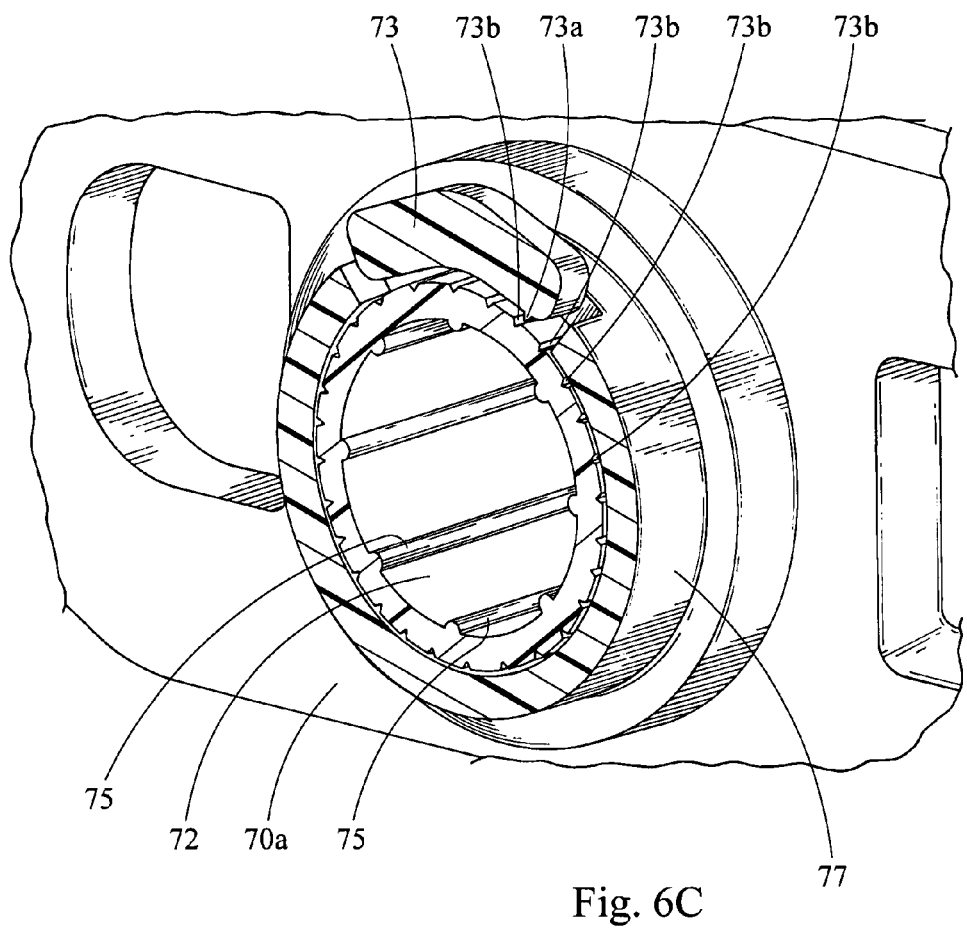
FIG. 6C is a front-view of an endoscope securing and positioning device.

FIGS. 6A and 6C depict another endoscope securing and positioning device 70 having a proximal portion 70A and a distal portion 70B. Endoscope securing and positioning device 70 maintains the position of elongated tubular body 71. In this embodiment, elongated tubular body 71 of endoscope is modified such that it contains locking grooves 74 as depicted in FIGS. 6A and 6B. Thus, when elongated tubular body 71 is inserted through lumen 72, grooves 74 engage with the locking teeth 75 (shown in FIG. 6C) of endoscope securing and positioning device 70. Grooves 74 engage with locking teeth 75 to prevent the rotational movement of elongated tubular body 71 but still allow for independent axial movement. Patient P bites with teeth T upon outer portion 76 of endoscope securing and positioning device 70 in order to prevent elongated tubular body 71 from damage due to teeth T. It is also contemplated that this device can contain air holes so that patient P can breath through the mouth M.

To rotate elongated tubular body 71, the medical professional releases button 73 and rotates race 77 until the desired position of elongated tubular body 71 is reached. Once the desired position is reached, the medical professional re-engages locking button 73 by rocking it so that button 73 locks race 77 into place by having protrusion 73A engage with one of the multiple grooves 73B (as shown in FIG. 6C). The dimension of grooves 73B is approximately 0.002" deep by 0.002" wide; however, other dimensions are contemplated. Because endoscope securing and positioning device 70 maintains the position of endoscope tube 71, the medical professional does not need to hold elongated tubular body 71 in the rotated position. A sleeve having a grooved outer service could be disposed about the endoscope as opposed to modifying the outer surface thereof.

Figure 7:
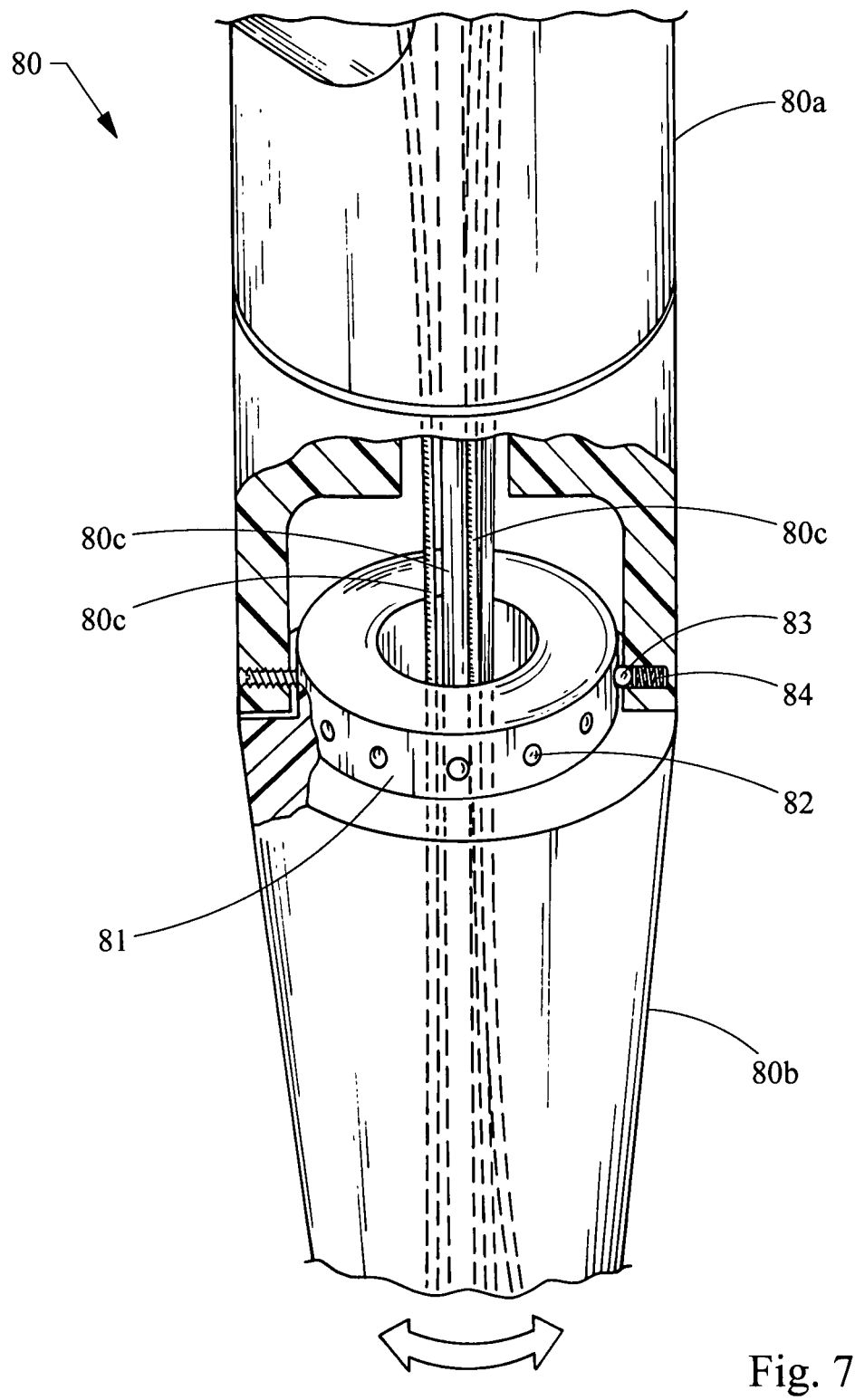
FIG. 7 is a front view of a modified endoscope.

FIG. 7 depicts a modified endoscope. Distal portion 80B of positionable endoscope 80 is rotatable relative to proximal portion 80A. Proximal portion 80A of positionable endoscope 80 is fixedly attached to coupling 81. Inside coupling 81 is a ball bearing 83, a spring 84 and bearing locks 82.

The medical professional rotates distal portion 80B of positionable endoscope 80 which causes spring 84 to decompress as ball bearing 83 rotates into one of the bearing locks 82. Once ball bearing 83 is secure in one of the bearing locks 82, the rotated position of distal portion 80B of positionable endoscope 80 will be maintained until sufficient rotational force is applied to distal portion 80B of positionable endoscope 80 to cause spring 84 to decompress and ball bearing 83 to rotate around into the next adjacent bearing lock 82. In order to avoid breaking the inner workings 80C of the endoscope (which may include traditional control devices for controlling a camera and for deflecting the tip of the endoscope), care should be taken not to rotate coupling 81 more than 180 degrees.

Figure 8:
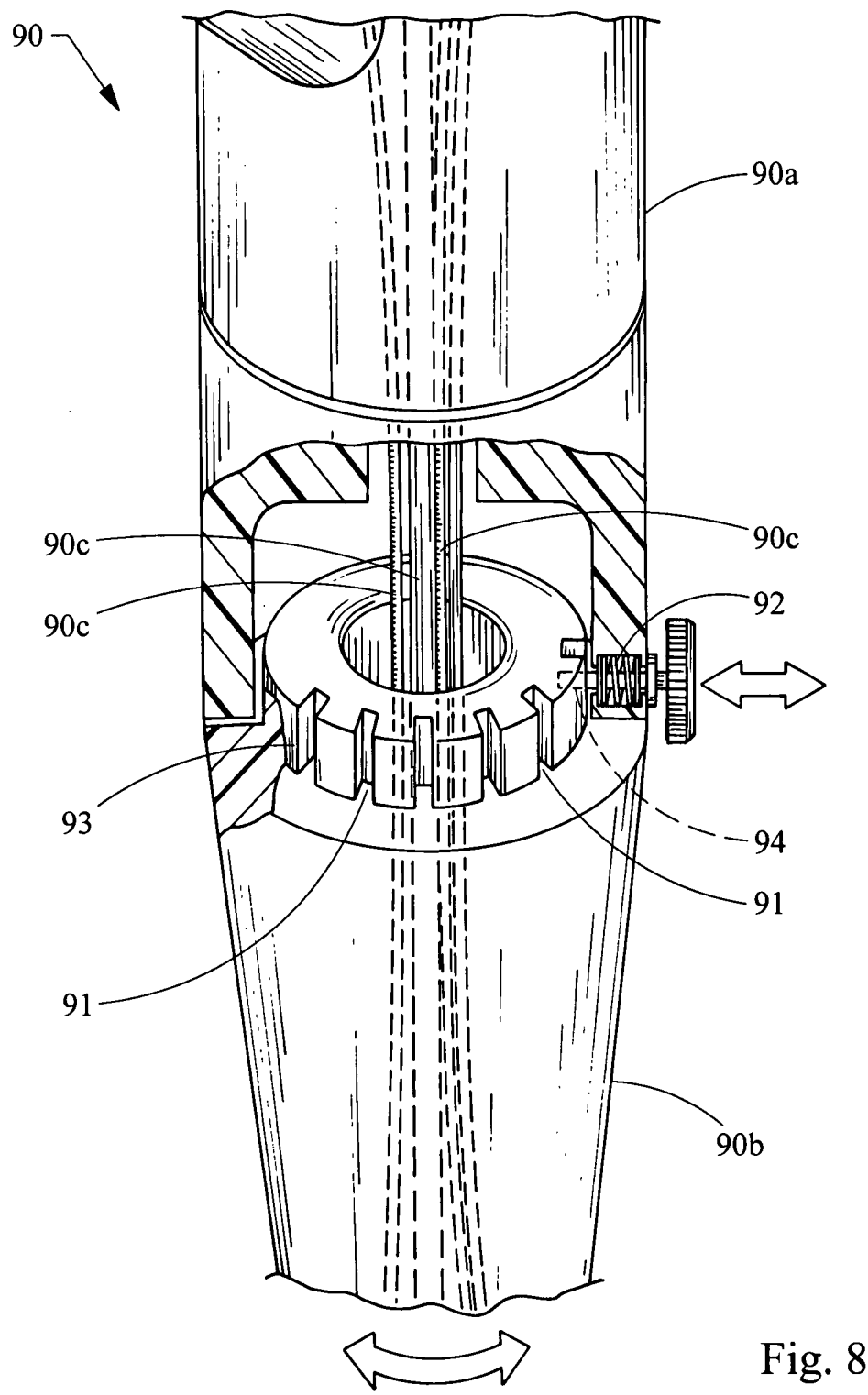
FIG. 8 is a front view of a modified endoscope.

FIG. 8 depicts another positionable endoscope 90 like that depicted in FIG. 7. Distal portion 90B of positionable endoscope 90 is rotatable relative to proximal portion 90A. Proximal portion 90A of positionable endoscope 90 is fixedly attached to coupling 93. Coupling 93 contains locking ridges 91 which engage with locking peg 94 which is attached to spring-loaded knob 92.

To rotate distal portion 90B of positionable endoscope 90, the medical professional pulls spring-loaded knob 92 to disengage it and rotates distal portion 90B of positionable endoscope 90. Once distal portion 90B is rotated into position, spring-loaded knob 92 is reengaged causing locking peg 94 to engage with locking ridge 91. In order to avoid breaking the inner workings 90C of the endoscope (which may include traditional control devices for controlling a camera and for deflecting the tip of the endoscope), care should be taken not to rotate coupling 93 more than 180 degrees.

Figure 9:
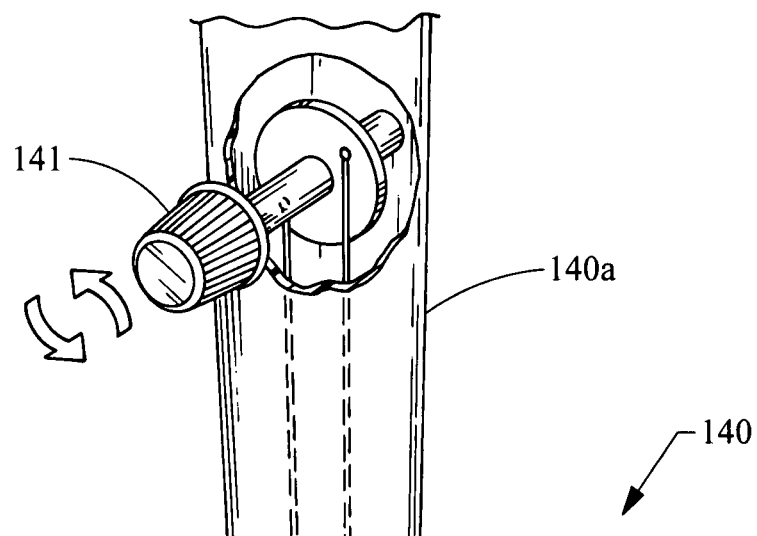
FIG. 9 is a perspective view of a modified endoscope.
Figure 9:
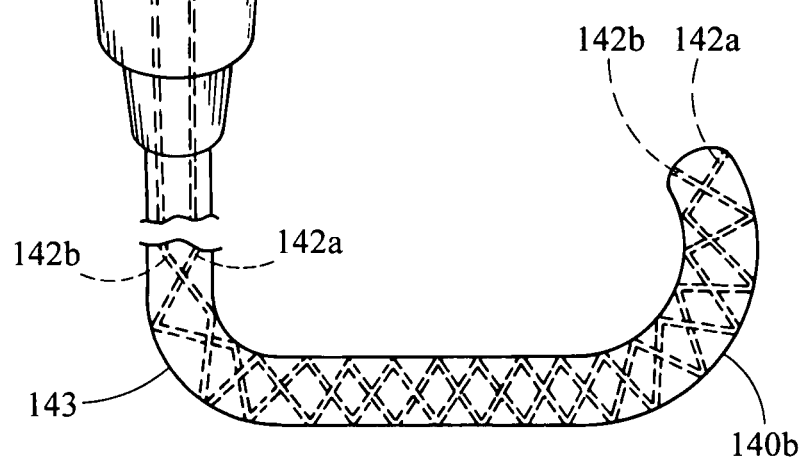

FIG. 9 depicts a modified endoscope that is able to deflect and rotate elongated tubular body 143. Positionable endoscope 140 is equipped with cables 142A, 142B that are located along the interior portion of the endoscope starting at wheel 141 through elongated tubular body 143 where they become spirally attached to elongated tubular body 143. Cables 142A, 142B are braided and made from stainless steel, although other configurations and materials are contemplated.

To use positionable endoscope 140, the medical device inserts distal end 140B of positionable endoscope 140 into the patient. To help position the device, the medical professional rotates wheel 141 counter-clockwise causing cable 142A to retract, thereby causing distal end 140B of elongated tubular body 143 to deflect and rotate in the direction that cable 142A pulls it. To un-deflect and un-rotate elongated tubular body 143, the medical professional rotates wheel 141 in the opposite direction until cable 142A is unwound causing elongated tubular body 143 to relax and straighten. To deflect the tip in the opposite direction, the medical professional rotates wheel 141 clockwise causing cable 142B to retract, thereby causing distal end 140B of elongated tubular body 143 to deflect and rotate in the direction that cable 142B pulls it. To un-deflect and un-rotate elongated tubular body 143, the medical professional rotates wheel 141 in the opposite direction until cable 142B is unwound causing elongated tubular body 143 to relax and straighten.

Figure 10:
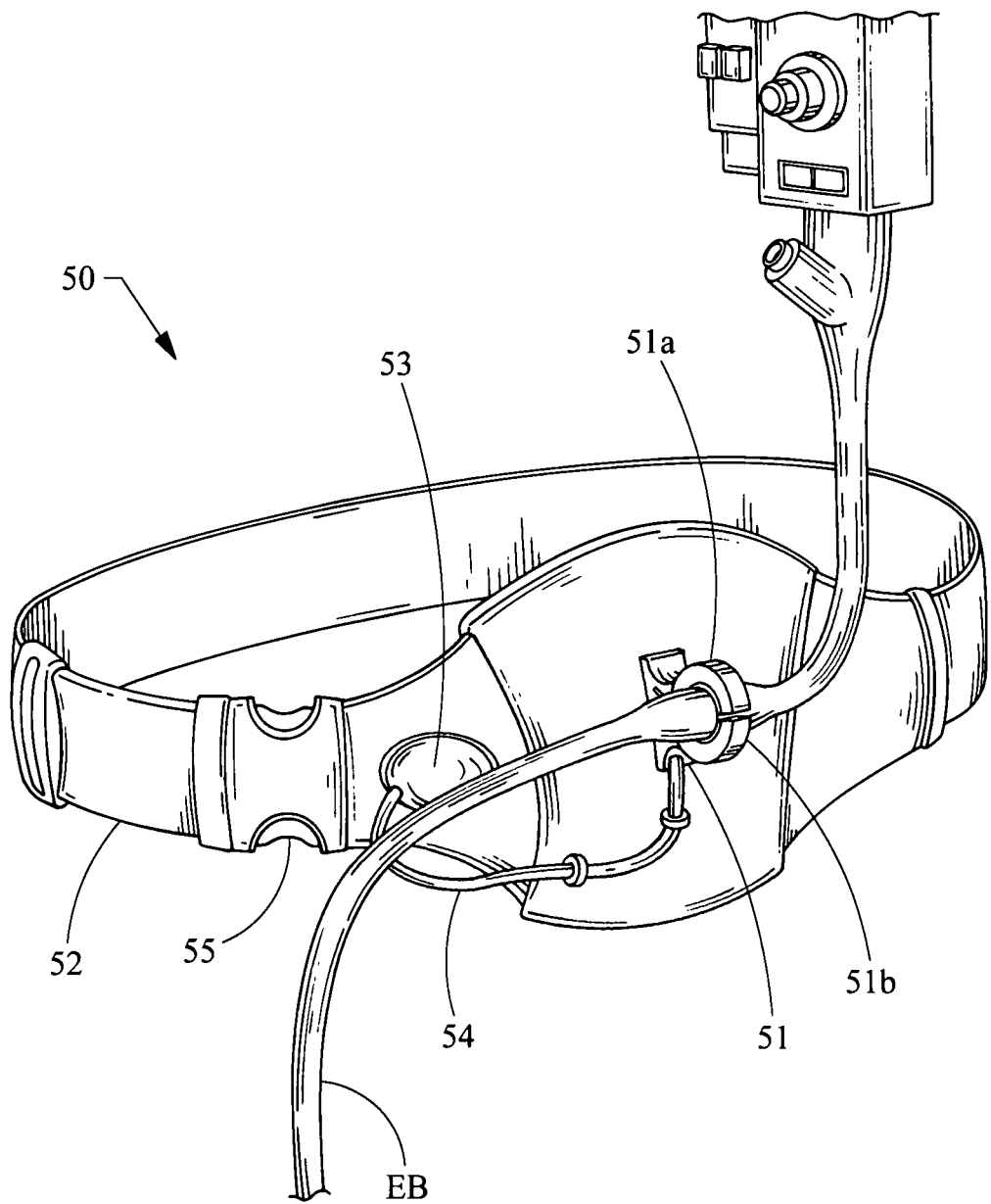
FIG. 10 is a front-view of an endoscope securing belt.

FIG. 10 is a front-view of endoscope securing belt 50. Endoscope securing belt 50 includes a clamp 51 having clamp arms 51A, 51B. Clamp 51 maintains the position of elongated tubular body EB of the endoscope. To use endoscope securing belt 50, the medical professional positions belt strap 52 around his/her waist and connects clasp 55. Belt strap 52 maintains the position of endoscope securing belt 50 onto medical professional when clasp 55 is engaged.

The medical professional disengages clamp 51 by pressing on clamp release bulb 53 that is connected to clamp 51 via a clamp release line 54. Clamp release bulb 53 and clamp release line 54 contain a fluid such as air. Compressing clamp release bulb 53 compresses the fluid inside. As it does so, a pneumatic force is created such that it causes clamp arms 51A, 51B to overcome the opposing force of a spring (not shown) and separate apart. Alternatively, instead of using a fluid, a mechanical drive cable could also be used to actuate/open clamp arms 51A, 51B.

When clamp arms 51A, 51B are disengaged, elongated tubular body EB of the endoscope may be freely positioned into an orifice of a patient. Once elongated tubular body EB of the endoscope is in position, the medical professional reengages clamp 51 by releasing clamp release bulb 53 causing clamp arms 51A, 51B to come together and hold elongated tubular body EB of the endoscope in place.

Figure 11A:
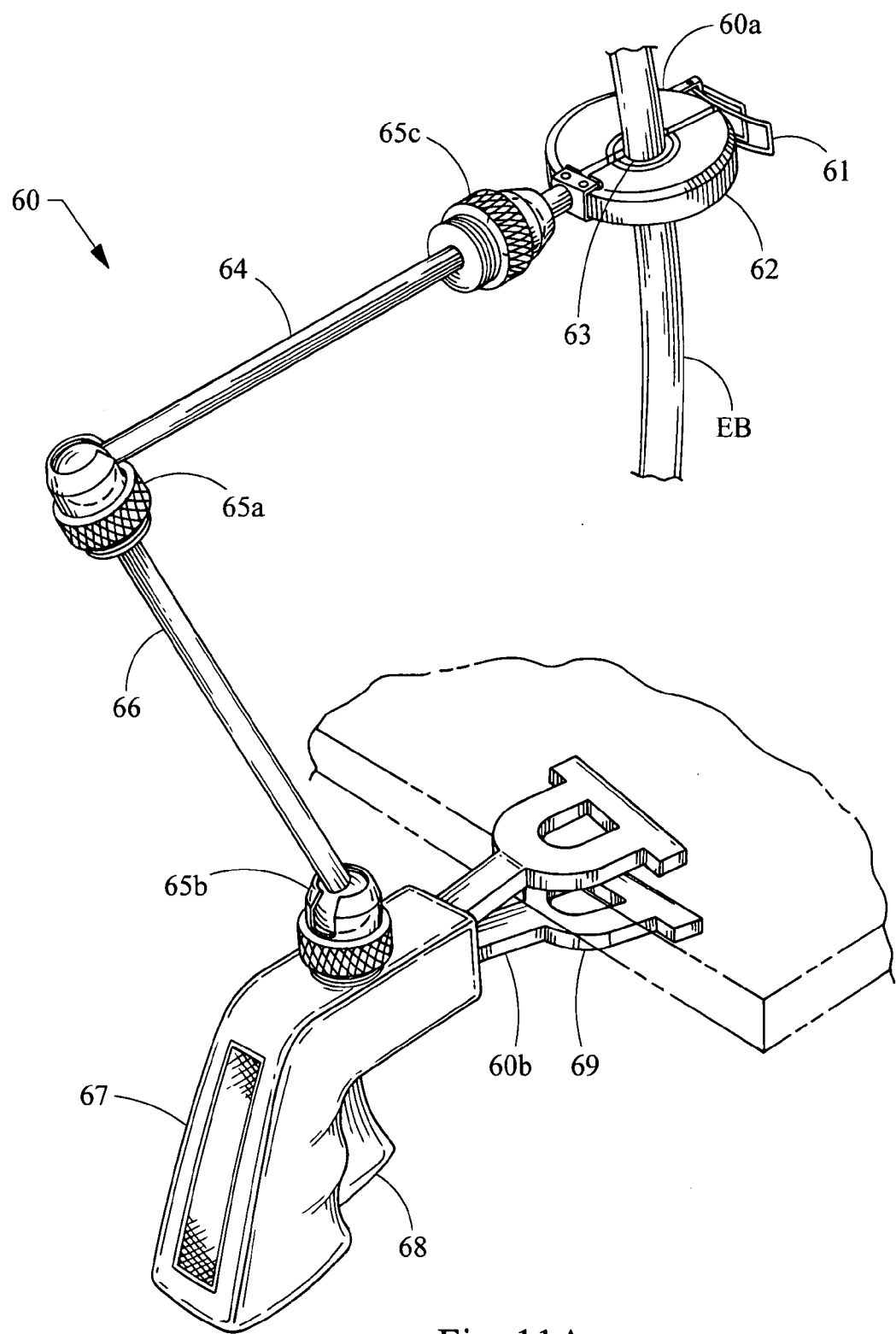
FIG. 11A is a side-view of an endoscope securing and positioning device.
Figure 11B:
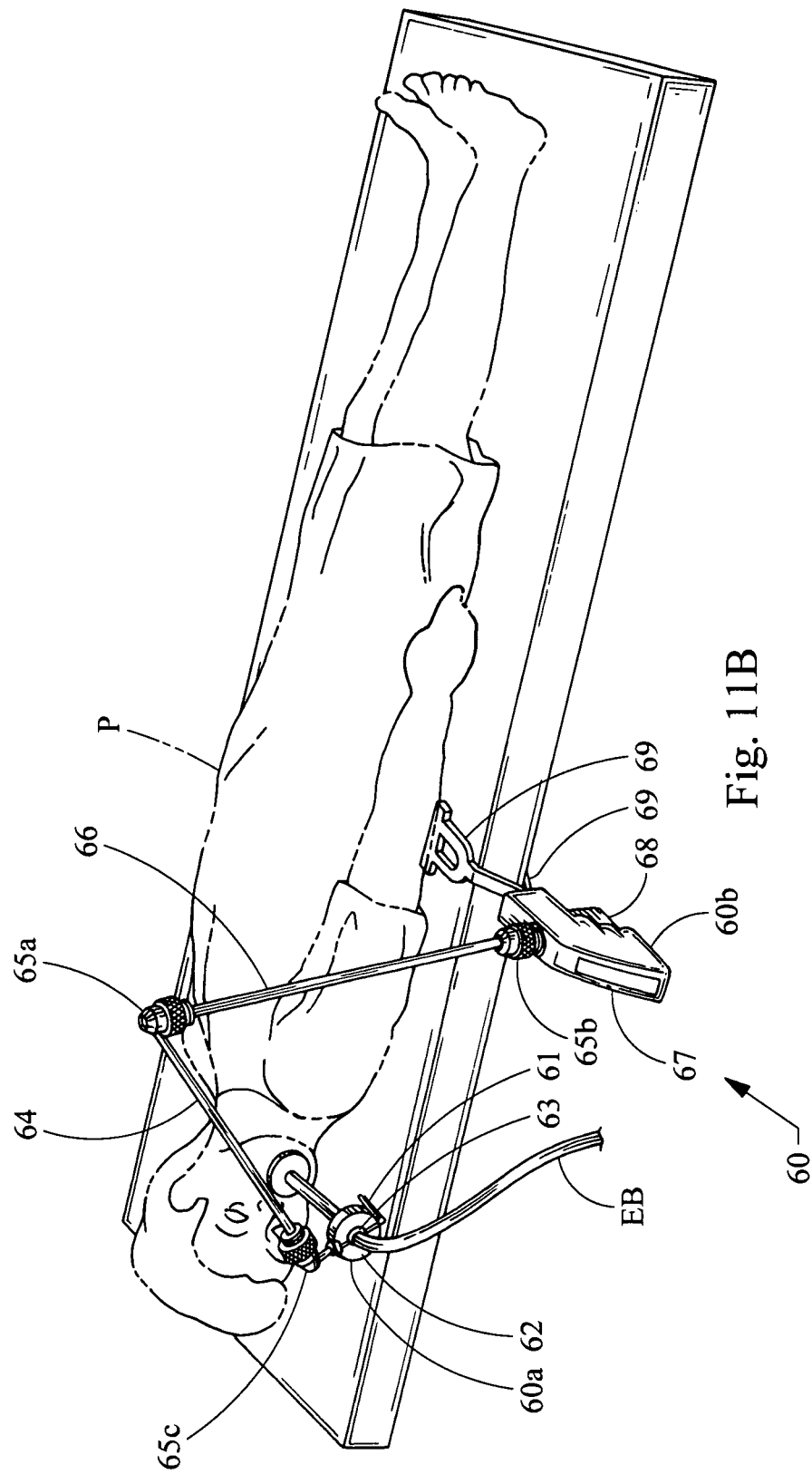
FIG. 11B is a side view of a patient depicting a use of the endoscope securing and positioning device.

FIGS. 11A and 11B depict another endoscope securing and positioning device 60. In FIG. 11A, endoscope securing and positioning device 60 is shown having a proximal portion 60A and a distal portion 60B. Endoscope securing and positioning device 60 maintains the position of elongated tubular body EB of endoscope. Located at distal end 60B of endoscope securing and positioning device 60 is bed clamp 69 that clamps to a bed, table, or any other stable item near patient. Engaging and disengaging bed clamp 69 is controlled by pulling trigger 68 that is attached to handle 67. Handle 67 is attached to arm 66 by lockable ball joint 65B to allow for rotation, lateral, and longitudinal movement of arm 66. Arm 66 is attached to arm 64 via lockable ball joint 65A to allow for the rotational, lateral, and longitudinal movement of arm 64. Alternatively, arms 64, 66 could also be a spring-loaded four-bar mechanism.

Clamp 62 is attached to arm 64 via lockable ball joint 65C to allow for rotational movement of clamp 62. Clamp 62 is lined with a rubber material 63 (polyurethane, polytetrafluoroethylene, other suitable polymers, and other suitable materials may also be used) in order to prevent damage to elongated tubular body EB of endoscope as well as to increase friction there between. Clamp lock 61 locks clamp 62 around elongated tubular body EB of endoscope.

FIG. 11B depicts a use of the device depicted in FIG. 11A. Here, clamp lock 61 is engaged, thus causing locking clamp 62 to maintain the position of elongated tubular body EB within patient P. To adjust elongated tubular body EB, the medical professional moves arms 64 or 66 into the proper position. To rotate elongated tubular body EB, clamp lock 61 is disengaged causing clamp 62 to open and release its hold on elongated tubular body EB. Once elongated tubular body EB is positioned EB, clamp lock 61 is reengaged. Use of endoscope securing and positioning device 60 is not limited to those endoscope that enter through the mouth.

Figure 12A:
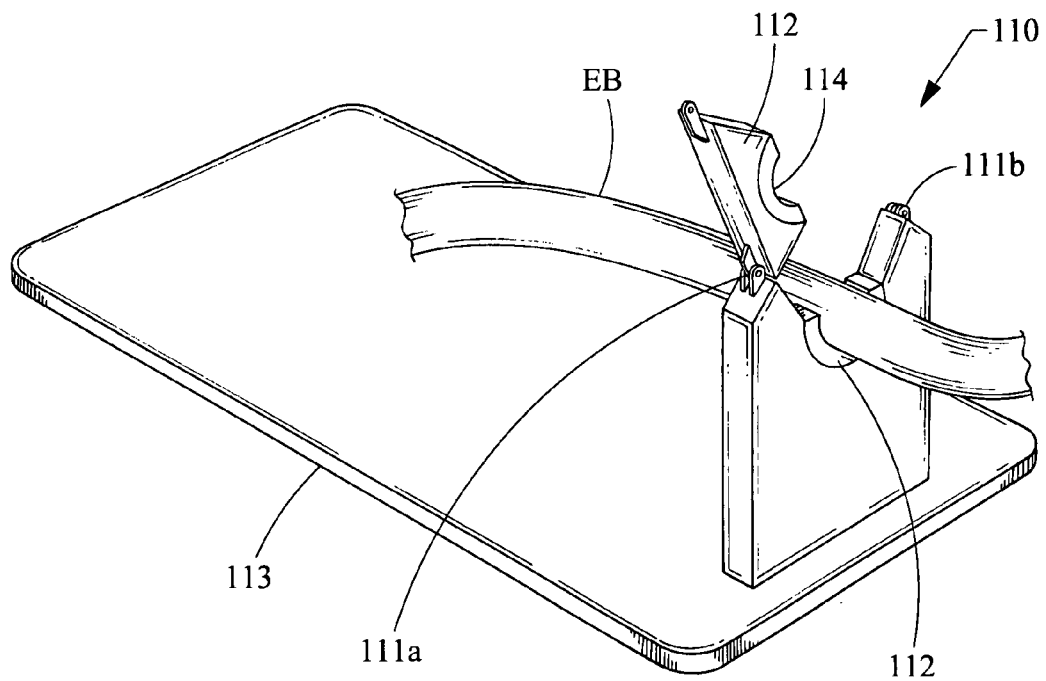
FIG. 12A is a perspective view of an endoscope securing and positioning device.
Figure 12B:
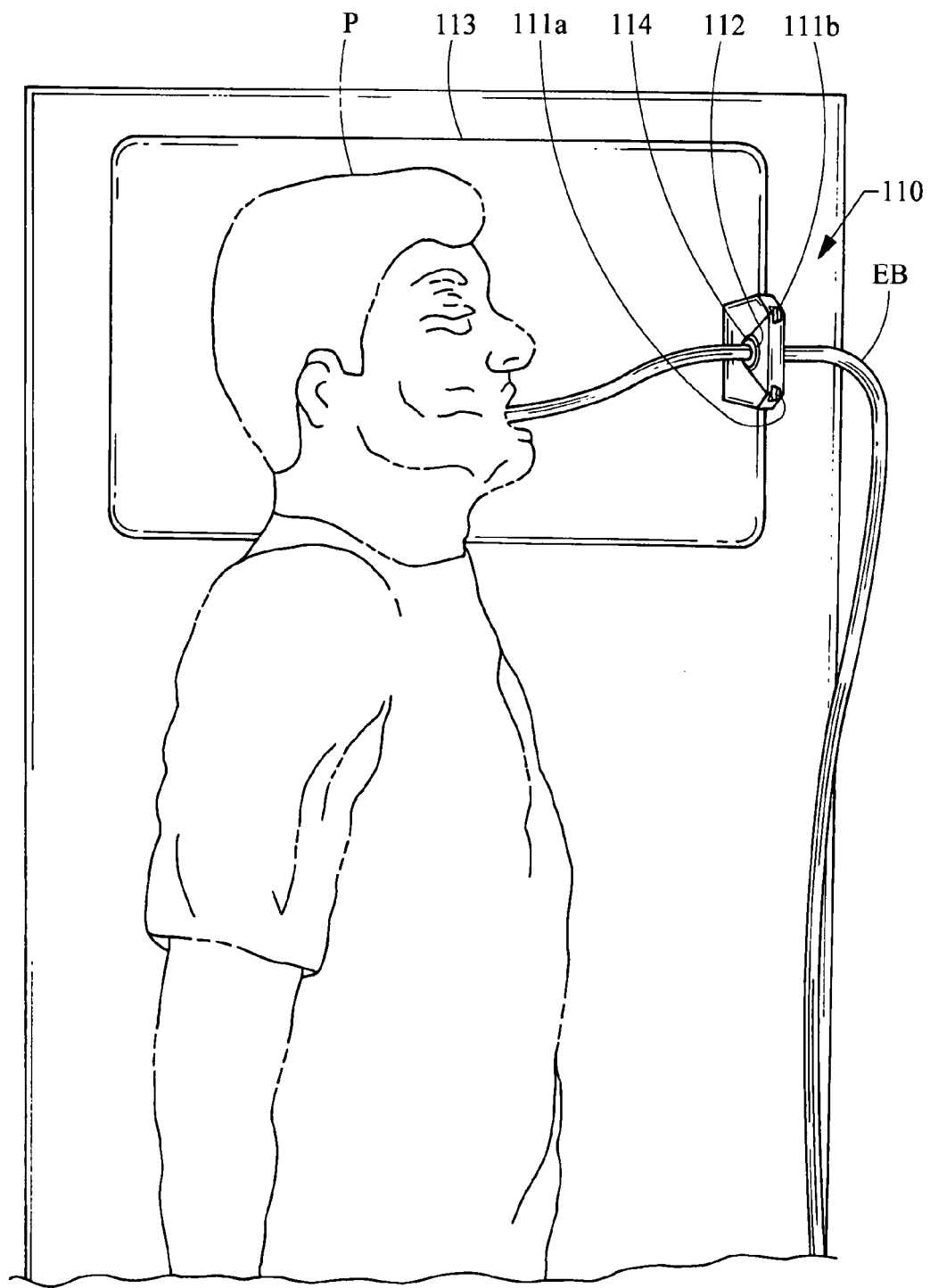
FIG. 12B is a side-view of a patient depicting a use of an endoscope securing and positioning device.

FIG. 12A depicts an endoscope securing and positioning device 110 that is shown in use in FIG. 12B. Endoscope securing and positioning device 110 includes a board 113 on which patent P rests. Board 113 is connected to a cuff 112 for securing and positioning elongated tubular body EB of endoscope. Cuff 112 is lined with a rubber material 114 (polyurethane, polytetrafluoroethylene, other suitable polymers, and other suitable materials may also be used) in order to protect the outside service of elongated tubular body EB from damage. When locked using locking hinge 111B, cuff presses against elongated tubular body EB preventing lateral and rotational movement. When locking hinge 111B is disengaged, cuff opens at hinge 111A and allows elongated tubular body EB to be repositioned. Board 113, cuff 112, hinge 111A, and locking hinge 111B can be made from a variety of materials including, but not limited to, polyurethane, polytetrafluoroethylene, other suitable polymers, stainless steal, and other suitable materials. Use of endoscope securing and positioning device 110 is not limited to those endoscopes that enter through the mouth.

Figure 13:
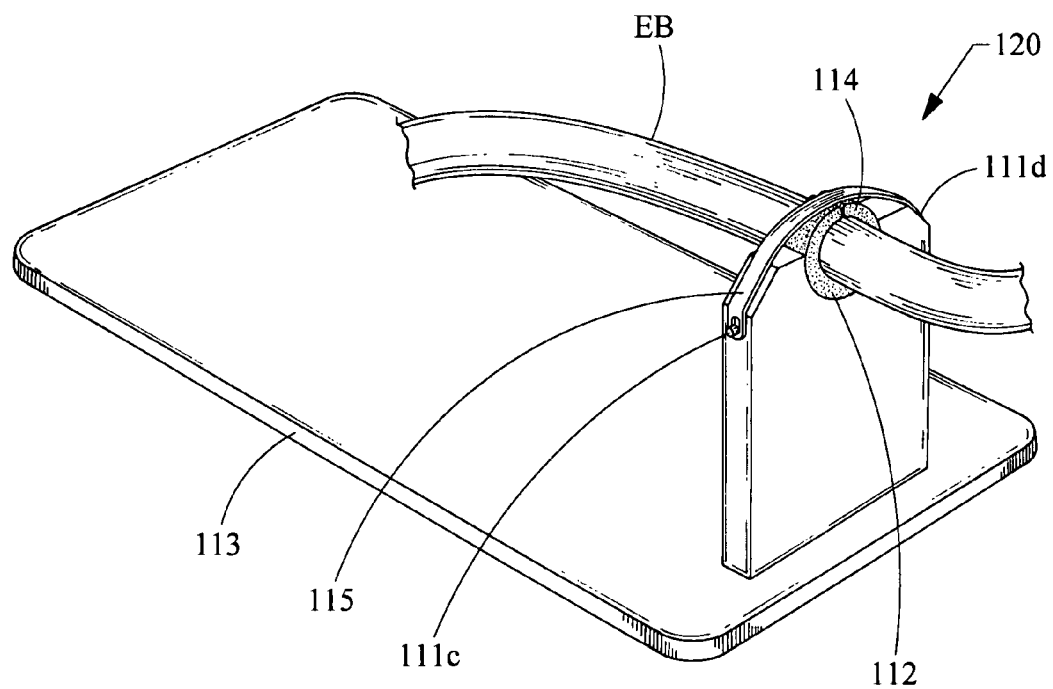
FIG. 13 is a perspective view of an endoscope securing and positioning device.

FIG. 13 depicts another embodiment of the endoscope securing and positioning device depicted in FIGS. 12A and 12B. Endoscope securing and positioning device 120 has a locking band 115 that removably attaches at 111C and 111D in order to prevent rotational and axial movement of elongated tubular body EB. Locking band 115 can be made from a variety of materials, including, but not limited to, rubber.

Figure 14A:
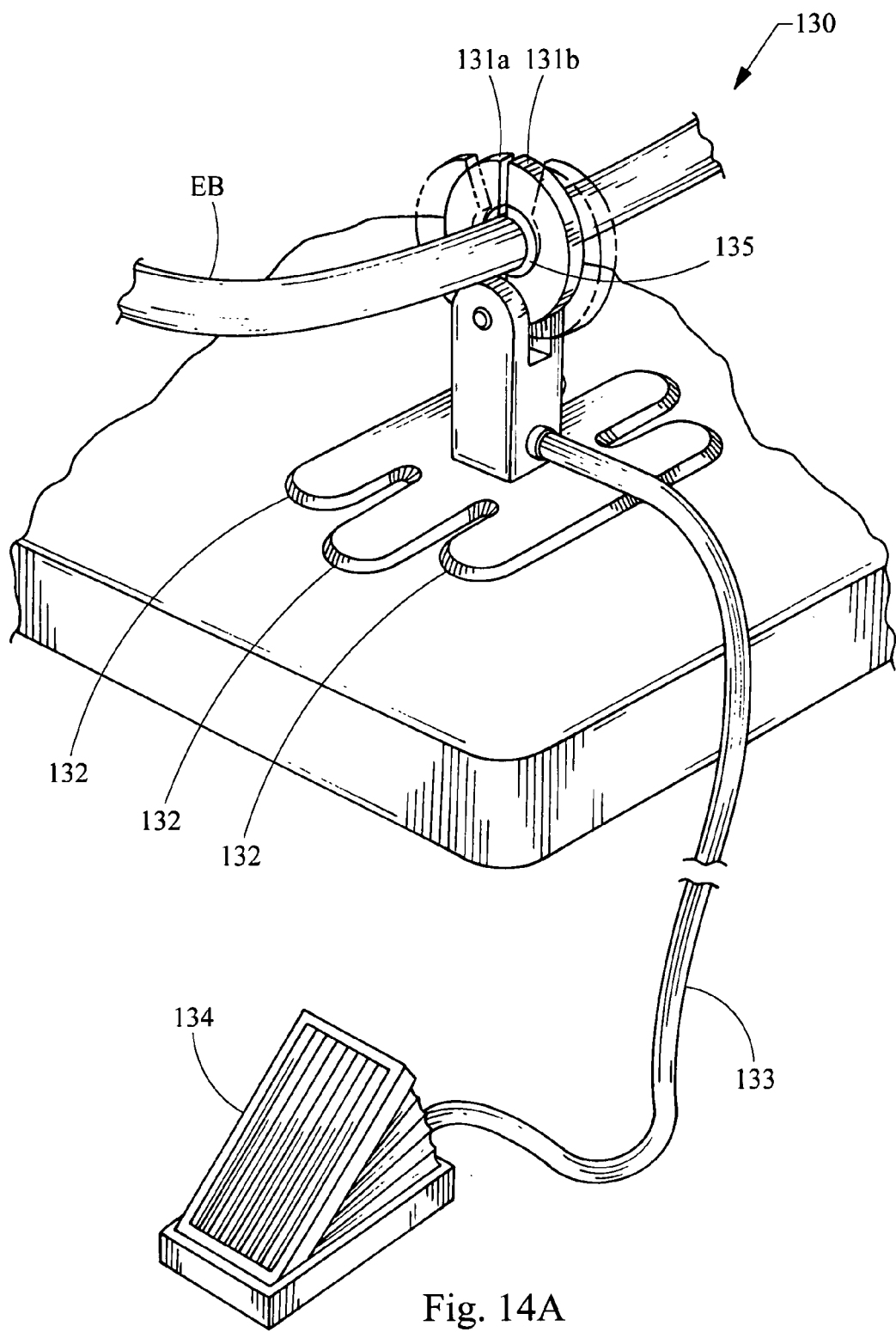
FIG. 14A is a perspective view of an endoscope securing and positioning device.
Figure 14B:
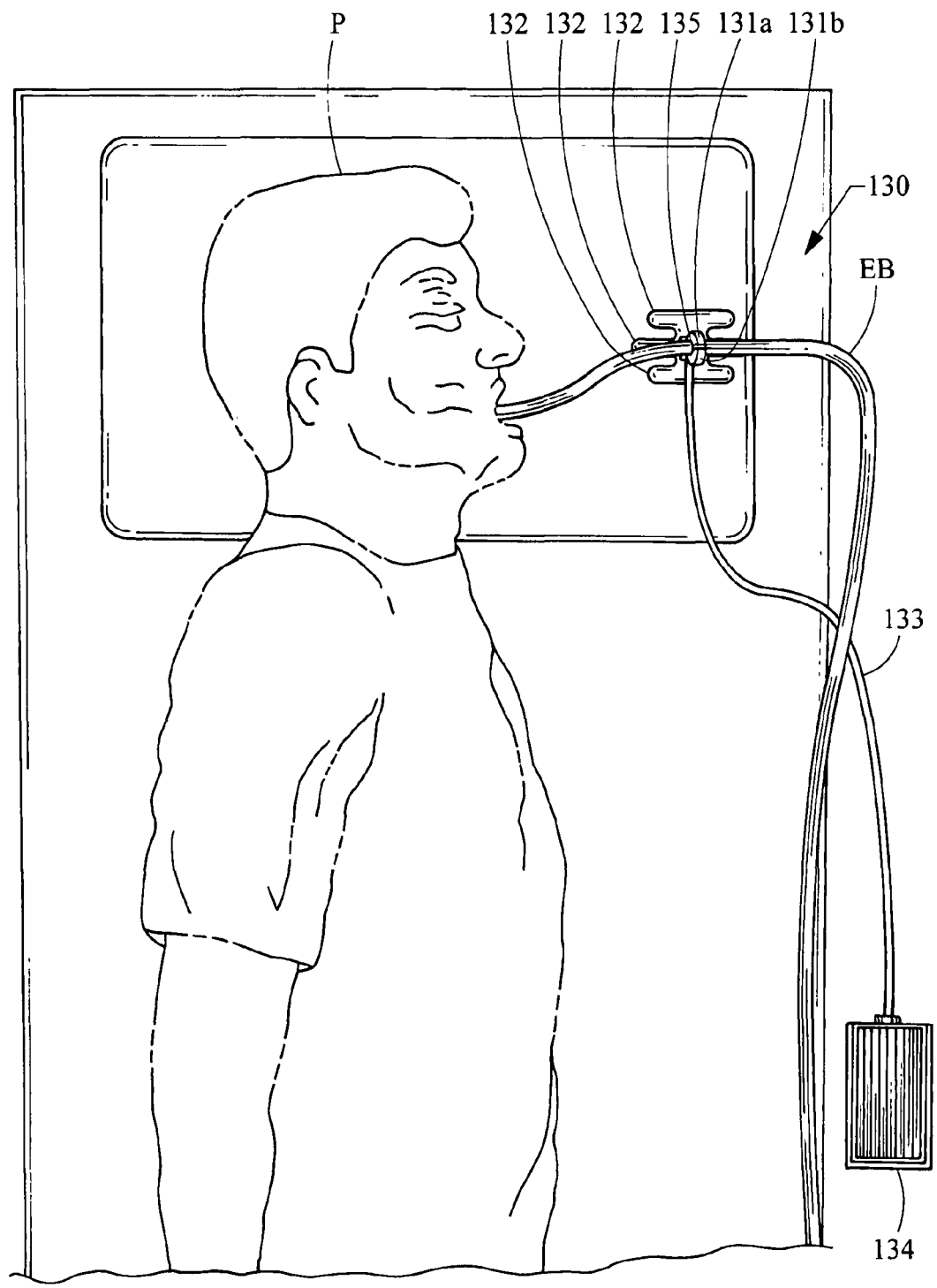
FIG. 14B is a side-view of a patient depicting a use of an endoscope securing and positioning device.

FIG. 14A depicts an endoscope securing and positioning device 130 that is shown in use in FIG. 14B. Use of endoscope securing and positioning device 130 is not limited to those endoscopes that enter through the mouth. Endoscope securing and positioning device 130 is placed near patient P. Endoscope securing and positioning device 130 has a clamp 131A, 131B that opens when foot pedal 134 is pressed, and closes when foot pedal 134 is released. Foot pedal 134 is connected via clamp release line 133.

Foot petal 134 and clamp release line 133 contain a fluid such as air. Compressing foot petal 134 compresses the fluid inside. As it does so, a pneumatic force is created such that it causes clamp 131A, 131B to overcome the opposing force of a spring (not shown) and separate apart. Alternatively, instead of using a fluid, a mechanical drive cable could also be used to actuate/open clamp 131A, 131B.

While foot pedal 134 pressed, elongated tubular body EB of endoscope is thread through clamp 131A, 131B and positioned. Once positioned, foot pedal 134 is released causing clamp 131A, 131B to close and maintain the position of elongated tubular body EB of endoscope. The interior surface of clamps 135 is lined with a rubber material (polyurethane, polytetrafluoroethylene, other suitable polymers, and other suitable materials may also be used) in order to prevent damage to elongated tubular body EB of endoscope as well as to increase friction there between. Feet 132 provide stability to endoscope securing and positioning device 130 to prevent it from tipping. Endoscope securing and positioning device 130 can be made out of many materials, including but not limited to, aluminum, stainless steel, polyurethane, polytetrafluoroethylene, other suitable polymers, and other suitable materials. Endoscope securing and positioning device 130 should be sufficiently heavy in order to maintain the position of elongated tubular body EB of endoscope. Thus, a weight of five pounds is generally sufficient although heavier or lighter devices are contemplated.

Figure 15:
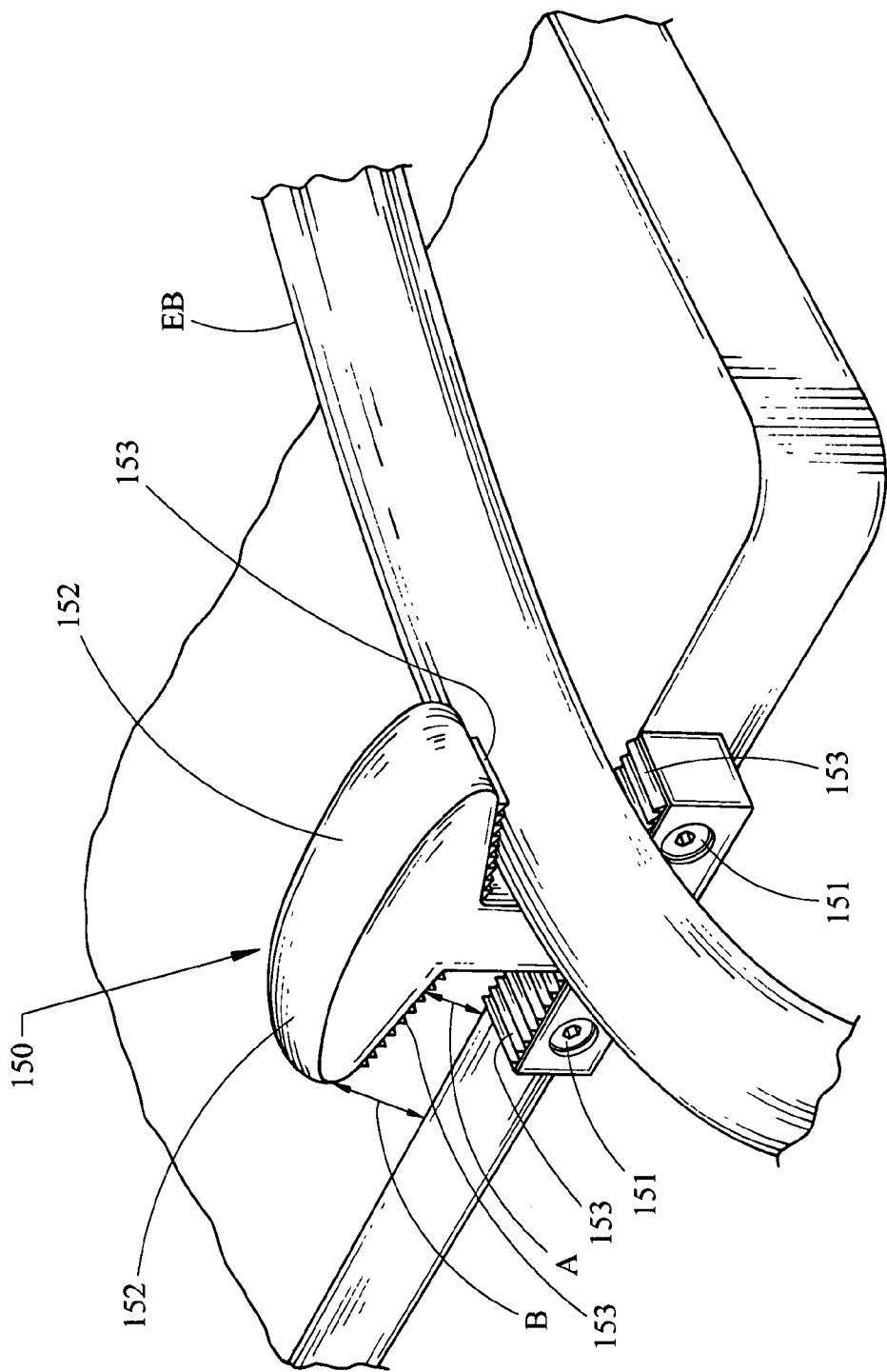
FIG. 15 is a perspective view of an endoscope securing and positioning device.

FIG. 15 depicts another embodiment of an endoscope securing and positioning device 150 that is attached to a bed or table via bolts 151. Although bolted in this embodiment, endoscope securing and positioning device 150 can be attached in a variety of different ways, including but not limited to, clamps. The gap at line A-A is about 10 mm whereas the gap at line B-B is about 20 mm. Greater or lesser gap distances can be used, however, the gap distance should be such that it holds elongated tubular body EB of endoscope in place. Endoscope securing and positioning device 150 can be made out of many materials, including but not limited to, aluminum, stainless steel, polyurethane, polytetrafluoroethylene, other suitable polymers, and other suitable materials.

To use endoscope securing and positioning device 150, the medical professional threads elongated tubular body EB of endoscope under arm 152. Arm 152 is shaped in such a way that as elongated tubular body EB of endoscope attempts to un-rotate itself, the arm 152 tightens and maintains the position of elongated tubular body EB of endoscope. Arm 152 is lined 153 with rubber (polyurethane, polytetrafluoroethylene, other suitable polymers, and other suitable materials may also be used) in order to prevent damage to elongated tubular body EB of endoscope as well as to increase friction there between. Endoscope securing and positioning device 150 may also include a threaded portion so that the gap distances (A-A, B-B) can be adjusted.

The foregoing description and drawings are provided for illustrative purposes only and are not intended to limit the scope of the invention described herein or with regard to the details of its construction and manner of operation. It will be evident to one skilled in the art that modifications and variations may be made without departing from the spirit and scope of the invention. Changes in form and in the proportion of parts, as well as the substitution of equivalence, are contemplated as circumstances may suggest and render expedience; although specific terms have been employed, they are intended in a generic and descriptive sense only and not for the purpose of limiting the scope of the invention set forth in the following claims.

What is claimed is:

1. A securing mechanism comprising:
   an endoscope having a handle and an elongated tubular portion extending from the handle, the elongated tubular portion comprising a plurality of axially extending grooves,
   an engagement portion adapted for engagement with the elongated tubular portion of the endoscope, the engagement portion comprising a plurality of teeth engaged with the grooves so as to secure the rotational position of the elongated tubular portion of the endoscope without inhibiting axial movement of the elongated tubular portion of the endoscope relative to the securing mechanism, wherein the engagement portion is rotatably disposed within a circular race of the securing mechanism,
   wherein the securing mechanism comprises a button adapted for selectively allowing or preventing rotation of the engagement portion relative to the circular race, and wherein the securing mechanism is configured for attachment to a patient, and further comprising a bite block having a proximal portion, a distal portion, an inner portion, and an outer portion, wherein the inner portion contains a lumen; wherein the engagement portion is disposed within the lumen of the inner portion.

2. The securing mechanism of claim 1 further comprising at least one air hole.

* * * * *